United States Patent [19]

Pugliese

[11] 4,049,830

[45] Sept. 20, 1977

[54] BOVINE TEAT DIP

[75] Inventor: Peter T. Pugliese, Bernville, Pa.

[73] Assignee: Milmark Research, Inc., Bernville, Pa.

[21] Appl. No.: 629,222

[22] Filed: Nov. 6, 1975

Related U.S. Application Data

[63] Continuation-in-part of Ser. No. 523,333, Nov. 13, 1974, abandoned, which is a continuation-in-part of Ser. No. 366,159, June 1, 1973, abandoned.

[51] Int. Cl.$^2$ .................... A01N 9/24; A61K 31/045; A61L 13/00
[52] U.S. Cl. .................................. 424/343; 424/170; 424/258; 424/274; 424/326; 424/330
[58] Field of Search ......................... 424/343

[56] References Cited

U.S. PATENT DOCUMENTS

| 3,137,623 | 6/1964 | Gessler | 424/170 |
| 3,210,248 | 10/1965 | Feldman et al. | 424/365 |
| 3,326,808 | 6/1967 | Noseworthy | 424/49 X |
| 3,535,427 | 10/1970 | Millar et al. | 424/170 X |
| 3,728,449 | 4/1973 | Cantor et al. | 424/150 |

FOREIGN PATENT DOCUMENTS

| 1,057,131 | 2/1967 | United Kingdom |

*Primary Examiner*—Leonard Schenkman
*Attorney, Agent, or Firm*—William H. Elliott, Jr.

[57] ABSTRACT

A bovine teat dip effective against both gram-positive and gram-negative bacteria, and containing lipids capable of reestablishing the natural lipid barrier or of forming a protective lipid barrier to foreign matter in the treated zone so as to minimize disruption of the natural defense mechanisms against infection or irritation.

5 Claims, No Drawings

BOVINE TEAT DIP

This application is a continuation-in-part of Ser. No. 523,333, filed Nov. 13, 1974 which is turn, is a continuation-in-part of Ser. No. 366,159, filed June 1, 1973, both now abandoned. This invention relates to a bovine teat dip for use in the dairy industry to control, prevent or treat bovine mastitis, and to a method of controlling, treating or preventing bovine mastitis.

Bovine teat dip preparations heretofore available, in the most instances, use glycerine as an emollient and contain a detergent and a germicide (usually iodine or chlorine) in an oil, a water, an oil-in-water, or a water-in-oil emulsion carrier. One such preparation is an oil-in-water emulsion of hydrolyzed coco butter (free fatty acids), glycerine, soap and hexachlorophene or dichlorophene.

The available preparations are subject to many disadvantages or objections; for example, the hydrolyzed coco butter dips do not stay in suspension, they settle rapidly, and must be vigorously shaken before each application in order to obtain a uniformity of dispersion. Further, in cold weather the coco butter dips exhibit a strong tendency to gel making application difficult. Some of the available preparations are undesirable for the reason that they contain or tend to precipitate salts or insoluble masses that hang up on the teat during the afterwashing and these salts or insolubles can cause irritation and are difficult to strip before milking. Some dips do not drain rapidly and in cold weather the residual or undrained water in the dip frequently freezes on the teat and udder to the great discomfort of the animal. Most available dips employ germicides that are only effective against gram-positive bacteria, hence they are not fully effective against the fauna and flora of teat which includes a wide spectrum of gram-negative bacteria, microorganisms and fungi. Dips in which elemental iodine, or non-ionic iodine complexes (also known as iodophores), are used as the germicide are not effective against most coliform bacteria and when they are used as teat dips it is exceedingly difficult to provide effective germicidal activity without developing teat skin irritants. The irritating character of the iodine dips is inherent therein. In order to keep the iodine complexed and in solution it is necessary that inorganic salts such as sodium iodide or potassium iodide be present in the dip. As the dip dries these inorganic salts are deposited on the teat skin and are skin irritants. Irritation also occurs because the iodine dips are far more acidic than the teat skin. To minimize reaction of iodine with the lipid emollient, the iodiphor dips should have a pH of 3.5 to 4.5. However on Nov. 3, 1975 standing the pH of the iodophor dip formulations drop significantly due to the formation of hypoiodous and hydriodic acid by reaction of the iodine with water; pH values as low as 1 have been found in the commercial formulations and such acid conditions cannot be tolerated.

Accordingly, it is one of the objects of this invention to provide a bovine teat dip having a pH approximating that of the teat skin and that is effective against a broad spectrum of gram-positive and gram-negative bacteria and that contains water-soluble lipids capable of reestablishing the natural lipid barrier (or forming a protective lipid barrier) to foreign matter in the treated zone and minimize disruption of the natural defense mechanisms against infection or irritation. The compositions also have a unique combination of other desirable properties including:

1. solubility or emulsifiability characteristics such that the lipid system will form a transparent emulsion and will not settle on standing and can be removed by a simple water wash without precipitating salts or other insolubles.
2. are free of inorganic salts and therefore will not leave or deposit a source of irritation on the teat skin after dipping;
3. drainability or viscosity characteristics such that all water in the dip will run off readily or evaporate after application even in cold weather, but not so rapidly that absorption or penetration of the germicidal component or the lipid barrier formers is reduced to an ineffective level or that the teat orifice cannot be effectively sealed.
4. good detergency but non-irritating and non-sensitizing to either humans or the animals; and
5. the emolliency, humectancy, penetrability and spreadability desired in cosmetic preparations - and particularly in hand lotions.

It is another object of this invention to provide a method for preventing or treating bovine mastitis by sealing the teat orifice with a soft non-irritating button or bead of a germicidal preparation containing water solubilized lipids that approximate the composition of the lipid layer on the teat surface and that will prevent ingress of infective agents into the streak canal.

The objects and advantages of this invention are obtained by a bovine teat dip comprising an oil-in-water emulsion having a pH of between about 5.0 and 5.8, a viscosity of from 4 to 10 centipoise (Brookfield) at body temperature said composition being free of inorganic salts and including a surfactant or emulsifying detergent system that is stable over a pH range of 3 – 6.5 and that is capable of buffering the pH of the emulsion at between about 5.0 and 5.8; a water-solubilized lipid system in the oil or dispersed phase that is stable at pH 5.0 to 5.8 and that approximates the composition of the lipid layer of the teat surface; and one or more non-irritating, water-soluble germicides that are stable at acid pH values and which are effective against both gram-positive bacteria and gram-negative bacteria.

Since the flora and fauna of a bovine teat include a broad spectrum of bacteria, microorganisms and fungi, it is important that the germicidal component be effective against both gram-positive and gram-negative strains. In addition, the germicide should be stable at acid pH values and not react with the lipids or the emulsion components, soluble in water, and be effective in the presence of non-ionic surfactants. In the concentrations of normal use, it should be non-irritating to skin and non-toxic to humans and mammals. The preferred germicide or anti-bacterial agent for use in accordance with the teachings of this invention is 2-bromo-2-nitro-propan-1,3-diol (sometimes referred to as Bronopol). It is preferably used in a concentration of about 0.2% (by weight) of the preparation for optimum kill-rate effectiveness. It should be noted, however, that at concentrations over about 0.5% it commences to show some toxicity to the skin. Other germicides that have been found to be effective for purposes of this invention are tribromoanilide, captan (N-trichloromethylthio-4-cyclohexene-1,2- dicarboxamide); 8-hydroxy quinolin sulfate; and chlorhexidiene acetate. In accordance with the invention, one or more such germicides, when compatible, can be used in combination in the formulation to broaden the spectrum of germicidal effectiveness.

As previously stated, the dip preparation has a pH between 5.0 and 5.8. These pH values are highly important because they are close to the pH value of the teat skin itself (5.0 - 5.6) and the natural defense mechanisms are most effective at that range.

The preparation includes a non-ionic surfactant or emulsifying-detergent system that is stable over a pH range of 3 to 6.5. This range is needed because during the manufacture of the emulsion the pH values encountered are not constant and can vary over this range. The surfactant, in addition to being non-ionic, should exhibit good stability and emulsifying properties for $C_{12}$ to $C_{22}$ fatty acids, good detergency, possess a buffering capability and be mild to the skin. In use, and after the dip has been applied to the teats and udder, it is necessary to wash the treated parts with water before the next milking. Therefore, the surfactant system must be capable of providing for more than mere emulsifying and detergent capabilities — in that it is also important for the surfactant to be stable in both hard and soft water and capable of being readily stripped from treated areas without adhering thereto and without leaving salts or insolubles on the treated areas. However, the formulation should have drainability and viscosity characteristics such that it can spread wet and adhere to the treated areas without draining so rapidly as to prevent reforming the lipid film barrier or to prevent effective absorption or penetration of the germicidal component. The water and any unabsorbed emulsion components carried thereby should be able to drain off rapidly so that water will not be adhering to the treated areas when the cow is turned out to pasture. Such drainability can be obtained if the viscosity of the emulsion is of from 4 to 10 centipoise at 37° C. (body temperature) and where viscosity will not increase to a point that will objectionably interfere with drainability at 0° C. The optimum performance is obtained where the viscosity is about 7 centipoise at 37° C.

As all of these capabilities cannot be obtained by the use of a single surfactant, it is generally necessary to employ a surfactant system composed of a plurality of surfactants, each of which is capable of providing for or augmenting a certain desired function or functions. In addition, as will be discussed hereinafter, the surfactant system functions can also be fortified by other dip constituents that are capable of serving to some extent or other in a dual capacity as emollients and surfactants, or as emollients and viscosity controlling agents.

A preferred non-ionic surfactant is lauryl (poly-1-oxapropene) oxaethane carboxylic acid — i.e., Akypo RLM 45. This material will function as an emulsifier, detergent, a viscosity control and has a further very important function as it is the principal buffer. Per se, it has a pH of 2 — 3 — i.e., below that desired in the final dip. It is not soluble in water but is dissociable therein. It can react with organic bases to form water-soluble salts. This also simultaneously adjusts (raises) the pH and in doing so does not precipitate insolubles. It is a very stable buffer at pHs below 7. A preferred organic base for adjusting the pH of Akypo RLM 45 is triethanolamine. Inorganic bases cannot be effectively used as they tend to develop inorganic salts which, when present in the dip, can provide a skin irritant. They are also undesirable because inorganic salts can cause insolubilization of some of the fatty acid components.

Another useful surfactant system component for compositions made in accordance with this invention is polyethoxycetyl ether — (Brij 58) — this compound does not hydrolyze in the emulsion and serves as a wetting agent, promotes drainability and spreadability and as a solubilizer for the lipid components. As it dries it provides a $C_{15}$ fatty acid — a desirable skin lipid.

The lipid component of the preparation should have a fatty acid composition and chain length corresponding to that of the fatty acids normally present on the teat skin that functions as an emollient and be capable of forming a lipid protective barrier to foreign matter on the skin areas that have been treated with the preparation. Further, if the natural lipid protective barrier is broken during milking, a factor that gives rise to after-milking trauma, cracking of the teat, irritation and susceptibility to infection, the preparations of this invention can reform the lipid barrier.

It is important that all the lipid components present in the emulsion be in a solubilized form and be capable of forming what are referred to as transparent emulsions in which the lipids are in a highly stable oil phase. It is also important that no substances (such as inorganic salts) be present in the emulsion that will either, on standing or upon drying of the emulsion, tend to hydrolyze or split off the solubilizing groups and cause settling or precipitation of free fatty acids.

The solubilized lipid for use as the emollient component in accordance with this invention can be provided entirely by certain water solubilized polyoxyethylene ethers of lanolin. The 75 mol polyoxyethylene ether of whole lanolin (sold under the trademark Solulan 75 by Amerchol — a unit of CPC International) and the corresponding 50% aqueous material (sold by Amerchol under the trademark Solulan L-575) are especially well suited for these purposes. Optionally the lipid component can be provided by a lipid mixture that contains ethoxylated $C_{12}$ to $C_{22}$ fatty alcohols, ethoxylated $C_{12}$ to $C_{22}$ fatty acids and water-soluble modified lanolin derivatives — (i.e., water-solubilized cholesterol). An important characteristic required of the solubilized lipid component, whether provided by a single lipid or by a mixture of lipids, is that, upon drying, the resulting lipid solids should retain their water-solubility and remain soft and tacky for prolonged periods — i.e., at least 12 to 24 hours or more. In other words, the lipid component should be one that will not hydrolyze upon drying to form water-insoluble free fatty acids.

The quantity of lipid material present in the preparation should be such that the film formed on draining of the emulsion should not cake or occlude on the teat surface or be so heavy as to prevent normal water transpiration. The lipid component added as such (i.e. distinguished from the lipids derivable from the surfactant and/or buffering sytems) preferably should comprise about 2 to 5% of the preparation's weight; and at between about 5 to 10% lipids, the objectionable characteristics previously noted begin to develop.

Solubilized lipids that are useful in forming lipid mixtures that have the desired properties include mixtures of fatty alcohols, ethoxylated pure fatty acids and water soluble modified lanolin derivatives such as water solubilized cholesterol and acetylated polyoxyethylene derivatives of lanolin.

The fatty alcohols soften the skin surface and provide the preparation with penetrability so as to reform or form the lipid protective layer — a preferred fatty alcohol for use in such lipid mixtures is ethoxylated isostearyl alcohol containing 20 mols of ethylene oxide (Aldol 66-E-20 manufactured by Ashland Chemicals Co.).

The ethoxylated pure fatty acids serve as the principal emollient and have superior solubility characteristics to the free fatty acids — their solubility enables the ethoxylated fatty acids to stay in solution and minimize gelling tendencies of the dip in cold weather. A preferred ethoxylated fatty acid for use in such lipid mixtures is Arosurf 1855-E-40 — an ethoxylated stearic acid (55%) prepared from tallow fat.

Other suitable materials for providing the solubilized fatty alcohols and ethoxylated fatty acids in such mixed lipid systems include Ethoxalan 50 (Malmstron Chemcial Co.) and Solulan 575 (Amerchol) — both of which are ethoxylated lanolin with free fatty acids.

The water-soluble cholesterol or modified lanolin derivatives in the oil phase are used for emolliency, for its moisturizing effect and for humectancy to retard the rate of water loss and help prevent crusts from forming. It is also one of the components concerned with forming the protective lipid layer. In mixed lipid systems a preferred water-soluble modified lanolin is a partially acetylated polyoxyethylene derivative of lanolin (Amerchol's Solulan 98) that is very soluble in aqueous solutions and exhibits good substantivity to skin. Another suitable modified lanolin is the fully acetylated polyoxyethylene derivative of lanolin (Amerchol's Solulan 97); this material is more hydrophobic than Solulan 98 and has greater substantivity for the skin.

Another lipid system component which is desirably present in the oil phase of mixed lipid systems to supplement Solulan 98 or Solulan 97 in providing emollience and in forming the lipid-protective barrier, but primarily to assist the moisture control function, is the water-soluble 24 mol ethyleneoxide ether of cholesterol that has been derived from lanolin and known as Solulan C24. This component also functions as a solubilizer and emulsifier for the other lipid components of the system.

Where necessary to increase the viscosity, compatible agents such as propyleneglycol or sorbitol can be included in the formulation quantities ranging up to about 10% of the emulsion.

The amounts of the various components used must necessarily be such as will provide the desired properties and, as is customary in the cosmetic art, quantities are not critical (except as to the germicidal component) and can vary widely without departing from the spirit of this invention.

The following examples illustrate preferred embodiments of the invention.

EXAMPLE 1

A bovine teat dip having the following composition:

| | Ingredient | Wt. % | |
|---|---|---|---|
| 1. | Arosurf 1855-E-40 | 0.5% | |
| 2. | Aldol 66 - E-20 | 0.5% | |
| 3. | Solulan C-24 | 0.5% | |
| 4. | Solulan 98 | 0.5% | |
| 5. | Brij 58 | 1.0% | |
| 6. | Akypo RLM 45 | 2.5% | |
| 7. | Bronopal | 0.2% | |
| 8. | Triethanolamine Q.S. to pH 5.2 – 5.5 | .5% | (approx.) |
| 9. | Water Q.S. | 100.0% | | was prepared by combining ingredients 1 to 6 inclusive in a steel jacketed vessel and heating to 65° C. to form the oil phase. Water was slowly heated in another vessel to 65° C. and the oil phase was added slowly thereto with stirring. Triethanolamine was then very slowly added to the emulsion and pH measurement taken frequently. The solution becomes clear at pH 5.3 (if the end point is missed, one should not attempt to back titrate). The clear solution is cooled to below 40° C. and the Bronopol is then added.

EXAMPLE 2

To the formulation of Example 1, 5% (by weight) propyleneglycol was added to the mix after combining the Akypo RLM 45 and before adding the Bronopol. After all the other ingredients had been added, the viscosity was raised from about 5 centipoise from that of the formulation in Exaple 1 — i.e., to approximately 8 centipoise at room temperature. The propyleneglycol also serves as a fungicide and prevents growth of fungi in the emulsion during storage.

EXAMPLE 3

By proceeding as in Examples 1 and 2, except that ingredients 1 and 2 were replaced with 7% (by weight) of a 50% solution of Ethoxalan 50 (i.e., 3½% by weight lipid solids), gave an emulsion having the same properties and characteristics except that its drying time was slightly increased.

EXAMPLE 4

By proceeding as in Examples 1 and 2 except that ingredients 1 and 2 were replaced with 7% (by weight) of a 50% solution of Solulan 575 (i.e., 3 ½% by weight lipid solids), gave an emulsion having the same properties and characteristics except that its drying time was slightly increased.

EXAMPLE 5

A bovine teat dip having the following composition:

| | Ingredient | Wt. % | |
|---|---|---|---|
| 1. | Ethoxalan 50 or Solulan 575 | 3½% | (solids) |
| 2. | Solulan C-24 | 0.5% | |
| 3. | Brij 58 | 1.0% | |
| 4. | Akypo RLM 45 | 2.5% | |
| 5. | Sorbitol | 7.0% | (solids) |
| 6. | Bronopol | 0.25% | |
| 7. | Triethanolamine Q.S. to pH 5.2 – 5.5 | .5% | (approx.) |
| 8. | FD&C Yellow #6 | 0.07% | | was prepared as described in Example 1 by combining ingredients 1 to 5 before adding the Bronopal and adding the yellow (FD&C Yellow 6) after adjusting the pH. The dye will color the teats of treated cows yellow, giving a check on which cows have been treated. The color strips off readily in the pre-milking wash. Other FD&C colors can be substituted for FD&C Yellow #6 if desired.

EXAMPLE 6

A bovine teat dip having the following composition:

| | Ingredient Wt. | |
|---|---|---|
| 1. | Brij 58 | .5% |
| 2. | Solulan 75 | 4.6% |
| 3. | Akypo RLM | 1.0% |
| 4. | Propylene Glycol | 8.0% |
| 5. | FD&C Color | 0.07% |
| 6. | Bronopol | 0.2% | sufficient organic base to adjust pH to 5.2 to 5.8 and additional water to bring volume to 100%.

The composition was prepared by combining ingredients 1 to 4 (ingredient 2 having been previously melted)

in a jacketed vessel heated to 52° – 55° C. The contents were agitated until mix was uniform. The mix was added to cold water (at least an equal volume). The FD&C color (usually FD&C Yellow 6) was added and agitation continued. The pH was adjusted with triethanolamine to bring pH to 5.0 to 5.8 as in Example 1. The solution is cooled to below 40° C., the Bronopal with constant agitation and water to bring composition to 100% is then added.

Dip preparations or emulsions of the foregoing examples are applied as a dip rather than by spraying or injection and are especially adapted (physically and chemically) to carry out the various functions of the process hereinafter set forth. A dip cup is filled with the emulsion to a depth of about 5 inches, and after milking the individual teats are sequentially immersed to the full length of the teat, held in the dip for 1 - 2 seconds, and the dip cup removed. When the teats are dipped into the emulsion, the viscosity of the emulsion and the hydrostatic pressure are such that a quantity of the emulsion will be forced into the teat orifice and the lower portions of the streak canal. Upon removal of the dip cup, the viscosity and drainability of the emulsion is such that the emulsion will drain off the teat (without washing) at a rate that will permit penetration and absorption of the lipid components and enable the lipid protective barrier to be formed or reformed. The teats and udders will be water free when the cow is turned out to pasture. In addition, a small quantity — a drop or so — of the emulsion is caused to collect at the teat end and when dried to seal the teat orifice. Because the lipids employed do not hydrolyze to drying to form free fatty acids, the orifice is sealed on drying of the emulsion with a soft, non-irritating beadlet or film of water soluble germicidal lipid material that will prevent ingress of infective agents into the streak canal. The beadlet will maintain its water solubility and tackiness over the time interval between milkings (normally 11 hours), and does not harden. It can be readily removed by washing with water before the next milking. This is an important new concept to the control of mastitis.

I claim:

1. A bovine teat dip free of inorganic salts and having a pH of between 5.0 and 5.8, a viscosity of from 4 to 10 centipoise at 37° C. and comprising an oil-in-water emulsion of the following ingredients expressed in parts by weight:

| | |
|---|---|
| polyethoxycetyl ether | 0.5% |
| 75 mole polyoxyethylene ether of whole lanolin | 4.6% |
| lauryl (poly-1-oxapropene) oxaethane carboxylic acid | 1.0% |
| propylene glycol | 8.0% |
| 2-bromo-2-nitropropan-1,3 diol | 0.2% |
| organic base as necessary to adjust pH to 5.0 to 5.8 | |
| water as necessary to bring total volume to | 100% |

2. A composition according to claim 1 which also includes a FD&C color.

3. A composition according to claim 1 wherein the organic base is triethanolamine.

4. A method of making the composition of claim 1 which comprises combining the ingredients other than the 2-bromo-2-nitropropan-1,3 diol and water; heating the so combined ingredients to 65° C. to form an oil phase; heating the requisite amount of water to 65° C. in a separate vessel; adding the oil phase slowly to the hot water with stirring; adding organic base slowly and without back titrating until pH is a 5.2 to 5.5; cooling to below 40° C.; and adding the 2-bromo-2-nitropropan-1,3 diol.

5. The method of controlling mastitis in dairy cattle which comprises immersing the cow's teats in a dip according to claim 1 coating the teat with the emulsion; forcing some emulsion into the teat orifice and into the lower portions of the streak canal by hydrostatic pressure, draining the excess emulsion from the teat without washing so as to form a protective lipid barrier, and permitting a small quantity of the emulsion to collect at and when dry to seal the teat orifice with a soft, tacky film or beadlet of water soluble lipid that maintains its tackiness for at least 12 to 24 hours but which can be removed by washing with water before the next milking.

* * * * *

UNITED STATES PATENT OFFICE
CERTIFICATE OF CORRECTION

PATENT NO. : 4,049,830
DATED : September 20, 1977
INVENTOR(S) : Peter T. Pugliese It is certified that error appears in the above-identified patent and that said Letters Patent are hereby corrected as shown below:

Col. 1, line 2, "is" should read --in--.

Col. 1, line 52, delete "Nov. 3, 1975".

Col. 6, line 10, "Exaple" should read --Example--.

Col. 7, line 40, "11" should read --12--.

Signed and Sealed this

Eighth Day of August 1978

[SEAL]

Attest:

RUTH C. MASON
Attesting Officer

DONALD W. BANNER
Commissioner of Patents and Trademarks